United States Patent [19]

Tsang et al.

[11] Patent Number: 4,663,286

[45] Date of Patent: May 5, 1987

[54] ENCAPSULATION OF MATERIALS

[75] Inventors: Wen-Ghih Tsang, Lexington; Ann W. Shyr, Newton Center, both of Mass.

[73] Assignee: Damon Biotech, Inc., Needham Heights, Mass.

[21] Appl. No.: 579,494

[22] Filed: Feb. 13, 1984

[51] Int. Cl.$^4$ ................. C12N 11/10; C12N 11/04; C12N 5/00

[52] U.S. Cl. ................. 435/178; 264/4.1; 264/4.32; 435/182; 435/240

[58] Field of Search ............ 435/174, 177, 178, 182, 435/240, 241; 264/4, 4.1, 4.3, 4.32, 4.33, 4.7; 424/34, 35, 94

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,582,799 | 4/1986 | Jarvis, Jr. | 435/178 X |

Primary Examiner—David M. Naff
Attorney, Agent, or Firm—Lahive & Cockfield

[57] ABSTRACT

A core material such as viable cells is encapsulated by gelling an alginate polymer with a polyvalent cation to form shape-retaining gelled masses containing the core material, expanding and hydrating the gelled masses by contacting the masses with an aqueous saline solution, and forming a membrane about the expanded gelled massed to form capsules by contacting the gelled masses with a polycationic polymer having a molecular weight greater than 3,000 daltons. Expanding before membrane formation, permits better control of permeability properties and uniformity of the membrane. The gelled masses within the membrane may be liquified by contacting the capsules with a chelating agent which is preferably ethylene glycol bis-($\beta$-amino ethyl ether)-N,N-tetra-acetic acid. A second membrane layer may be formed by contacting the capsules with a second polycationic polymer. The second membrane may be coated with a polyanionic polymer such as alginate.

51 Claims, No Drawings

ENCAPSULATION OF MATERIALS

BACKGROUND OF THE INVENTION

This invention generally relates to encapsulation of core materials, including viable cells, within an intracapsular volume defined by a semipermeable membrane. More particularly, the invention relates to a process for producing large quantities of capsules having uniform membranes with improved porosity control adapted to promote growth of cells within the capsules.

U.S. Pat. No. 4,352,883, issued Oct. 5, 1982, upon application of Dr. Franklin Lim, discloses a basic procedure for encapsulating core materials, including viable cells, within capsules having semipermeable membranes. Viable cells encapsulated with the Lim procedure are capable of on-going metabolism, including mitosis, and secrete materials they would normally secrete in their unencapsulated form. Capsules made with the Lim technique may be engineered to have membranes which are permeable to molecules below a particular molecular weight but substantially impermeable to higher molecular weight molecules and to cells. The pores of the membranes are believed to comprise tortuous paths defined by the interstices of the membrane structure. Passage of molecules above a particular molecular weight is hindered by these tortuous path pores, and. above a certain higher molecular weight and corresponding effective molecular dimension, the hindrance is sufficiently great that the membrane is substantially impermeable to these molecules.

Porosity control is an important factor in a number of important uses of such microcapsules. The microcapsule membrane can be used for differential screening, that is, to separate molecules on a molecular weight basis. For example, U.S. Pat. No. 4,409,331, issued Oct. 11, 1983, discloses a method wherein substances secreted by cells within the capsule may traverse the membrane while other, higher molecular weight materials are confined within the capsules. Such capsules can simplify greatly collection of a substance of interest. Copending application Ser. No. 485,472, filed Apr. 15, 1983, now U.S. Pat. No. 4,582,799, discloses a process wherein cells producing a substance of interest which is not secreted may be lysed within the capsule membrane. Low molecular weight substances of interest can diffuse across the membrane into the extracapsular medium while cell debris and high molecular weight substances and contaminants, e.g., pyrogens, are trapped within the intracapsular volume.

The selective screening properties of the capsule membrane also allow the capsules to be used for cross-strain in vivo growth of hybridomas, as disclosed in copending application Ser. No. 579,460, filed Feb. 13, 1984, now abandoned. The capsule membrane permits cross-strain hybridomas to be grown within a body cavity of an animal whose immune system would normally attack the hybridomas. Astute engineering of membrane permeability properties allows high specificity collection of the secreted substance.

Effective membrane permeability control also permits the use of implanted capsules containing cells which secrete an antigen as an immunizing agent. The screening properties of the membrane produce relatively pure antigen as the immunizing agent without the need of a tedious antibody purification procedure and can lead to stimulation of specific antibody production.

Capsules with such membranes can also be used as part of a cell screening procedure. Extracapsular medium is tested for a substance secreted through the membrane. Contaminants having a molecular weight greater than the substance are kept within the capsule thereby reducing false positive results.

Application Ser. No. 579,460 No. DBH-455) was filed on even date herewith. This disclosure and the disclosure of U.S. Pat. No. 4,352,883 are incorporated herein by reference.

A preferred embodiment of the Lim encapsulation technique involves the formation of shape-retaining gelled masses which contain the material to be encapsulated, followed by deposition of a membrane on the surface of the gelled masses. The membrane is formed as relatively high molecular weight materials contact the gel masses and form ionic cross-links with the gel. Lim discloses that lower molecular weight cross-linking polymers permeate further into the structure of the gelled masses and result in a reduction of pore size. Lim also discloses that the duration of membrane formation affects pore size. Given a pair of reactants, the longer the cross-linking polymer solution is exposed to the gelled mass, the thicker and less permeable the membrane.

While the techniques for porosity control and membrane formation disclosed in the Lim patent can form acceptable membranes, many of the foregoing applications of the capsule technology could be improved if membranes having improved porosity control and better uniformity could be produced. The Lim porosity control techniques do not allow fine tuning of the membrane porosity, but rather set rough differential filtering limits.

In addition to improved porosity, for commercial purposes it is also important to be able to consistently produce microcapsules in large numbers having defect-free membranes. In this regard, membranes formed by the Lim techniques occasionally have protruding portions of cells or have cells anchored on the capsules. The Lim techniques also may produce capsules containing voids which allow cells, the substance of interest, or unwanted contaminants to escape from the capsule. If some small fraction of the microcapsules made with a specific purpose in mind have membrane voids, many of the objectives and advantages of the processes would be frustrated. Accordingly, modifications of the encapsulation processes which promote membrane uniformity and avoid random membrane defects are advantageous to commercial practice of many of the foregoing processes.

Accordingly, it is object of this invention to improve porosity control of microcapsule membranes. Another object is to promote more uniform membrane formation. A further object is to develop a process allowing formation of membranes which optimize cellular growth and secretion of substances produced by the cells. Still another object of the invention is to provide a process for producing permeable capsule membranes having more precise permeability limits and for reproducibly engineering such limits. Other objects and features of the invention will be apparent from the following.

SUMMARY OF THE INVENTION

The present invention constitutes an improvement on the Lim technique for encapsulating a core material within an intracapsular volume defined by a membrane.

Practice of the invention can provide improved membrane uniformity and porosity control, and can make the capsules more suitable for culturing cells.

As disclosed in the Lim patent, core material is suspended in a solution of a water-soluble polyanionic polymer capable of being gelled, and the polymer-core material suspension is formed into droplets or other discrete shapes. The droplets then are exposed immediately to a solution of polyvalent cations to produce soft, shape-retaining, hydrated gelled masses. In accordance with this invention the gelled masses, for purposes herein after set forth, are next expanded and further hydrated by contact with an aqueous solution which removes a portion of the polyvalent cations, e.g., saline solution. Thereafter, a membrane is formed about each of the expanded gelled masses by reaction between anionic groups on the polyanionic polymer hydrogel and cationic groups on a polycationic polymer having a molecular weight preferably greater than about 3,000 daltons. The preferred polyanionic polymers are acidic polysaccharides, most preferably alginate salts. Useful polycationic cross-linking polymers include proteins and polypeptides having plural reactive nitrogen-containing cationic groups, e.g., primary amines, polyvinyl amines, aminated polysaccharides, water-soluble salts thereof, and mixtures thereof. The currently preferred polycationic polymer is polylysine. Polyglutamine and polyornithine can also work well. A second membrane layer may be formed about the first by reaction with another polycationic polymer. Any of the cited cationic materials may be used to form the second membrane. The identity of the reactant and the molecular weight of the polycationic polymer or polymers used are selected to determine the porosity characteristics of the capsules. It has also been discovered that the charge density of the polycationic polymers used can have a material effect on porosity control.

The core material may be viable cells, such as genetically modified cells, e.g., hybridomas, eukaryotic cells, including animal tissue cells, or prokaryotic cells. The process may also include the step of postcoating the membrane with a water-soluble polyanionic polymer, e.g., alginate, which reacts with residual cationic sites on the membrane. The gelled masses may be reliquified after membrane formation by reaction with a chelating agent. Ethylene glycol bis-(β-amino ethyl ether)-N,N-tetra-acetic acid and salts thereof (EGTA) are the chelating agents of choice when the capsules are intended for use in growing cells. In this regard, it has been discovered that reliquification with EGTA has the effect of significantly enhancing cellular production of biological materials with the capsules as compared with other chelates such as EDTA or citrate.

Proper selection of reactants and reaction conditions permits formation of membranes of relatively specific permeability. For example, membranes may be engineered to be substantially impermeable to molecules having a molecular weight greater than about 150,000 daltons, and therefore substantially impermeable to all common immunoglubulins. The membranes may be permeable to molecules having a molecular weight up to about 500,000 daltons while precluding passage of higher molecular weight materials. Such capsules permit escape of IgG while retaining IgM. Alternatively, the membranes may be engineered to be permeable to molecules having a weight greater than 500,000 daltons but substantially impermeable to cells.

If, for example, a molecular weight cut-off at or below 150,000 daltons is sought, a second membrane may be formed about the capsules with a polycationic polymer having the same, or preferably a higher charged density than a first polycationic polymer, e.g., a polylysine membrane may be post-treated by immersion in a polyornithine or polyvinyl amine solution. If the membrane is to be permeable to molecules of a weight greater than 500,000 daltons, a high molecular weight cross-linking polymer such as a polylysine having a molecular weight greater than 200,000. daltons may be used. Practice of the gel expansion step in accordance with the invention significantly improves capsule membrane uniformity and enhances the efficacy of the porosity control techniques.

DESCRIPTION

As previously noted, the present invention permits improved control of membrane porosity and promotes the formation of more uniform membranes. The invention is based in part on the observation that gelled masses comprising polyanionic polymers, e.g., alginate, can be expanded or contracted by changing the degree of hydration of the polymer. The gel masses contain more than 98% water and are essentially soft, shape-retaining balls having a cross-linked gell lattice. It has been discovered that expanding the gel masses after gelling and before membrane deposition permits one to control better the permeability properties and uniformity of the membranes. Immersing the gelled mass in a solution of monovalent cations, e.g., saline, one or more times will remove a portion of the crosslinking polyvalent cations from the gel and increase the hydration state thereby expanding the gel lattice. Such treatment results in the production of uniformly hydrated gel masses well suited for the subsequent membrane deposition step. In the absence of such treatment, the gel masses vary in size and properties because the first formed masses have been immersed in the gelling solution longer than the last formed masses. Another important observation is that equilibrating the gelled mass with a solution containing polyvalent cations such as a calcium chloride solution will contract the gelled mass. A further phenonemon which has been discovered is that once a membrane has been formed about a gelled mass, immersion of the capsule in a monovalent cation solution will stretch the membrane, increasing the pore size. These phenomena, coupled with the observation that higher charged density crosslinkers tend to reduce pore size, make it possible to control more precisely the membrane permeability. When these observations are coupled with the permeability control techniques disclosed in the aforementioned Lim patent, there is provided to those skilled in the art a set of parameters which enable production of uniform capsules of consistent and more precise permeability properties.

As disclosed in the Lim patent, the core material is suspended in a solution containing a water-soluble, reversibly gellable polyanionic polymer, preferably sodium alginate, and the polymer-core material suspension is formed into droplets using conventional means, e.g., a jet-head droplet forming apparatus. The jet-head apparatus consists of a housing having an upper air intake nozzle and an elongate hollow body friction fitted into a stopper. A syringe, e.g., a 10 cc syringe, equipped with a stepping pump is mounted atop the housing with a needle, e.g., a 0.01 inch I.D. Teflon-coated needle, passing through the length of the housing. The interior of the housing is designed such that the tip of the needle is subjected to a constant laminar airflow which acts as an air knife. In use, the syringe full of the solution containing the material to be encapsulated is mounted atop the housing, and the stepping pump is activated to incrementally force drops of the solution to the tip of the needle. Each drop is "cut off" by the air stream and falls approximately 2.5-3.5 cm into a gelling solution where it is immediately gelled by absorption of cross-linking ions. The preferred gelling solution is a calcium ion solution, e.g., 1.2% (w/v) calcium chloride. The distance between the tip of the needle and the calcium chloride solution preferably is set to allow the polymer-core material solution to assume the most physically favorable shape, a sphere (maximum volume/surface area). Air within the tube bleeds through an opening in the stopper. The gelled, shape-retaining spheroidal masses or temporary capsules, which preferably are between 50 microns and a few millimeters in diameter, collect in the solution as a separate phase and can be recovered by aspiration.

In accordance with the invention the gelled masses are then expanded by one or more separate immersions or washings in a monovalent cation solution, e.g., saline. This immersion removes a portion of the cross-linking calcium ions, and further hydrates the gel. The gelled masses thus expand to provide better coverage of the core material, i.e., the solid phase core material does not protrude through the surface of the gel masses. Solid phase core material which is anchored to the exterior of the gel is removed by the saline wash. Therefore, only core material in the interior of the gel is encapsulated.

The saline washes also promote more uniform capsule membranes by equilibrating the amount of calcium ions crosslinking the alginate lattice of the gel masses. The gel masses are not all formed simultaneously; the droplets which encounters the calcium bath early in the cycle spend a longer time in the bath and therefore retain more calcium ions in the gel structure than those late in the cycle. The saline washes remove more calcium ions from the higher density masses (the early gelled droplets) than from the lesser density gel masses thereby equilibrating the calcium content of the gel masses.

Membranes formed about expanded gel masses are also less prone to rupture due to stresses caused by degelling. It appears that the expanded lattice network may have more resiliency which allows better compensation for degelling stress.

A membrane is then formed about the expanded gelled mass by reaction between cationic groups on the expanded, gelled polyanionic polymer, and anionic groups on a polycationic polymer, e.g., polylysine. The polycationic polymer may have a molecular weight as low as 3,000 daltons, but polylysine of 35,000 daltons or higher molecular weight is preferred. After the membrane is formed about the expanded gelled masses, other steps are utilized to fine tune the porosity of the membrane. For example, a series of washes in a saline solutions will expand the pores of the membrane while a series of washes in a calcium chloride solution will contract the pores. A second membrane layer may be formed about the capsules using an additional polycationic polymer, e.g., by exposure to a polyornithine solution or exposure to a higher charged density polymer such as polyvinyl amine. This technique may be used to decrease pore size.

As disclosed in the Lim patent, the intracapsular volume preferably is reliquified by immersion of the capsules in a solution of a chelating agent. Chelating agents which have been used with success include ethylene diamine tetra-acetic acid (EDTA), sodium citrate, sodium succinate, and most preferably, ethylene glycol bis-($\beta$-amino ethyl ether)-N,N-tetra acetic acid (EGTA). If sodium citrate is used as the chelating agent, voids may form in the capsule membranes as the membranes take an irregular shape in response to the pressure of citrate. The membrane returns to its original shape as the citrate approaches equilibrium with the intracapsular volume, but if the core material is a living cell sensitive to citrate, cell growth or the cells' ability to produce biological materials may be impaired. In contrast, immersion of a capsule in EGTA solution appears to cause the membrane to fold inwardly and remain in this altered configuration until the EGTA is removed. As described in Example 4, infra, it appears that cells grow better and are metabolically more active in capsules treated with EGTA as opposed to citrate or other chelating agents tested.

As disclosed in the Lim patent, post-coating the capsules with a solution of a polyanionic polymer, e.g., sodium alginate, substantially removes the tendency for the capsules to clump. The anionic polymer reacts with residual cationic sites on the membrane causing negative surface polarity. As is known in the prior art, negative surfaces may inhibit growth and attachment of cells. Such growth can hinder intracapsular cell growth or adversely affect permeability. Additionally, immersing the capsule in a neutralizing agent such as 2-N-cyclohexylamino ethane sulfonic acid (CHES) or other zwitterion buffer may reduce the reactivity of and improve the capsule membrane.

The following non-limiting examples will further illustrate the processes of the invention and their advantages.

EXAMPLE 1

The following procedure may be used to produce capsules substantially impermeable to molecules having a molecular weight greater than about 150,000 daltons. A hybridoma, which produces IgG (molecular weight about 160,000 daltons), was used in this experiment.

Approximately 2.1 liters of a suspension containing about $2.2 \times 10^6$ cells/ml in 1% (w/v) sodium alginate (NaG-Kelco LV) was transferred to a jet-head apparatus, as previously described, and droplets were formed by forcing the suspension through sixteen 22 gauge needles at a rate of approximately 50 ml/minute. The droplets fell approximately 3 cm into 5 liters of a 1.2% (w/v) calcium chloride solution, forming gelled masses which were collected by aspiration and transferred to a 10 liter flask containing approximately 5 liters of isotonic saline for gel expansion. The saline was removed and replenished twice. In total, the saline expansion took approximately 11 minutes. Next, a membrane was formed about the gelled masses by contact with 5 liters of a 750 mg/l poly-L-lysine (Sigma Chemical Company, 65,000 dalton molecular weight) in isotonic saline solution. After 12 minutes of reaction, the resulting capsules were washed for 10 minutes with 5 liters of a 1.4 g/l solution of CHES buffer (Sigma) containing 0.2% (w/v) calcium chloride in saline. The capsules were washed for approximately 8 minutes with 5 liters of 0.3% (w/v) calcium chloride in saline, a second membrane was formed about the capsules by a 10 minute reaction in 5 liters of a 150 mg/l polyvinyl amine (Polyscience, 50,000–150,000 dalton molecular weight) in saline. The capsules were washed again with two 5 liters volumes of isotonic saline, over 7 minutes and postcoated with a 7 minute immersion in 5 liters of $5 \times 10^{-2}\%$ (w/v) NaG in saline solution. The capsules were washed for an additional 4 minutes in 5 liters of saline then the intracapsular volumes were reliquified by two immersions in 5 liter volumes of 55 mM sodium citrate in saline solution, the first for 10 minutes and the second for 6 minutes. As disclosed in Example 4, infra, replacing the sodium citrate solution with an EGTA solution would improve antibody yield. The capsules were washed twice in 5 liters of saline and washed once for 4 minutes in RPMI medium. The capsules were then allowed to grow in the growth medium, RPMI plus 10% fetal calf serum. IgG collects within the capsules and only trace quantities can be detected in the extracapsular medium. Capsules prepared according to this procedure are accordingly substantially impermeable to IgG but permit free tranverse of required nutrients thereby permitting cell growth and antibody production within the intracapsular volume.

EXAMPLE 2

This example illustrates a procedure for forming capsules which are permeable to IgG (molecular weight about 160,000 daltons) but substantially impermeable to IgM (molecular weight about 900,000 daltons). The cell used was a human-human hybridoma 77 from the National Institute of Health which produces and secretes human IgM.

Four hundred ml of a solution containing $1 \times 10^6$ cells/ml in 1% NaG (w/v) were formed into droplets using a bunch of eight 22 gauge needles in a jet-head apparatus as previously described. The feed rate was approximately 30 ml/minute and the distance from the needle tip to the gelling solution, 1 liter of 1.2% (w/v) calcium chloride, was about 3 cm. The gelled masses were washed three times with 1 liter volumes of isotonic saline over an 8 minute period and immersed for 10 minutes in 1 liter of 750 mg/ml of poly-L-lysine (Sigma, 65,000 dalton molecular weight) to form a permanent membrane. The resulting capsules were washed for 5 minutes in 1 liter of 1.4 g/l CHES containing 0.2% (w/v) calcium chloride in saline, then washed for 5 minutes with 1 liter of 0.3% (w/v) calcium chloride in saline solution. Capsules were expanded for 4 minutes with 1 liter of saline then post-coated for 7 minutes in 1 liter of $3 \times 10^{-2}\%$ (w/v) NaG in saline. The post-coated capsules were washed for 5 minutes in a 1 liter of saline solution then the intracapsular volumes were reliquified by two 6 minute immersions in 1 liter of a 55 mM sodium citrate in saline solution. The citrate was removed by two washes with saline, 1 liter each, and the resulting capsules were washed for 5 minutes in RPMI medium. The capsules were then suspended in one liter of medium (RPMI plus 20% fetal calf serum and antibiotics), and the cells therein were allowed to grow. The extracapsular medium was sampled. By assay it was determined that the extracapsular medium contained no IgM, showing that the capsules were substantially impermeable to molecules having 900,000 dalton molecular weight.

EXAMPLE 3

This example discloses a procedure for forming capsules which are permeable to IgM (molecular weight about 900,000 daltons) but impermeable to cells. Two hundred ml of a 1% (w/v) solution of NaG (Kelco LV) and the hybridoma cells of Example 2 were formed into droplets through five 26 gauge needles in a jet head apparatus as previously described. The resulting droplets fell approximately 2.5 cm into the gelling solution, 1 liter of 1.2% (w/v) calcium chloride, at a rate of 9.5 ml/m. The resulting gelled masses were expanded by three immersions in 0.5 liter volumes of saline and a permanent membrane was formed by a 10 minute reaction with 0.5 liter of one g/l poly-L-lysine (Sigma, average molecular weight about 260,000 daltons). The capsules were washed for five minutes in 0.5 liters of a 1.4 g/l CHES-saline solution containing 0.6% (w/v) calcium chloride and for an additional five minutes in 0.5 liters of 0.8% (w/v) calcium chloride in saline solution. The capsules were then washed once in 0.5 liters of saline and post-coated with 0.5 liters of 0.03% (w/v) NaG. The post-coated capsules were washed for 5 minutes in 0.5 liters of saline and the intracapsular volume was reliquified by two 5 minute washes, 0.5 liters each, of 55 mM sodium citrate. The capsules were washed once in saline, once in basal medium, and suspended in basal medium containing 20% fetal calf serum plus antibiotics. IgM was found to traverse the capsular membrane but cells were retained showing that the membrane is permeable to molecules of at least 900,000 molecular weight but is impermeable to cells.

EXAMPLE 4

This example demonstrates that the metabolic activity of encapsulated cells can be greatly enhanced by proper selection of the chelating agent used to reliquify the intracapsular volume. Four different chelating agents were tested: EDTA, EGTA, sodium citrate and sodium succinate, using encapsulated IgG producing Li8 hybridoma as a test system. The capsules were made following the procedure set forth in Example 1 except the sodium citrate of Example 1 was replaced with the concentrations of the chelating agents listed below.

TABLE 1

| Degelling Reagent | Conc. (mM) | Total Cell # at (day) | Days of Culture | end Culture µg/ml (day) |
|---|---|---|---|---|
| EDTA | 55 | $1.0 \times 10^6(6)$ | 6 | 0 |
| EGTA | 55 | $4.3 \times 10^7(17)$ | 27 | 1026 |
| Citrate | 55 | $2.3 \times 10^7(16)$ | 19 | 366 |
| EGTA | 55 | $3.5 \times 10^7(16)$ | 19 | 741 |
| Succinate | 55 | $2.3 \times 10^7(16)$ | 19 | — |
| EGTA | 55 | $3.6 \times 10^7(19)$ | 21 | 939 |
| EGTA | 36 | $4.1 \times 10^7(19)$ | 21 | 892 |
| EGTA | 28 | $3.7 \times 10^7(19)$ | 21 | 734 |
| EGTA | 28 | $9.3 \times 10^7(27)$ | 27 | 659 |
|  |  | $5.3 \times 10^7(20)$ |  | 578(20) |
| EGTA | 28 | $6.0 \times 10^7(27)$ | 27 | 693 |
|  |  | $4.1 \times 10^7(20)$ |  | 590(20) |
| EGTA | 14 | $7.3 \times 10^7(27)$ | 27 | 887 |
|  |  | $5.4 \times 10^7(20)$ |  | 780(20) |

Table 1 illustrates that the EGTA is the best chelating agent for cell growth and results in improved antibody production as compared with citrate approximately by a factor of 2.

The remaining entries in Table 1 illustrate experiments to determine the optimum EGTA concentration for degelling and antibody production. As is evident from the data, it appears that 36 mM and 55 mM concentrations of EGTA are approximately equivalent in promoting antibody production while lower concentrations of EGTA yield lower antibody concentrations despite having roughly identical cell growth.

EXAMPLE 5

This example illustrates the effect of using multiple saline washes to expand the gel masses prior to membrane formation. The same capsule formation procedure and hybridoma as described in Example 1 was used except the number of saline washes conducted before membrane formation was modified. After capsule formation, the encapsulated hybridomas were grown for 20 days in the culture medium and the total cell count and intracapsular antibody concentration was measured. Table 1 gives the results of this experiment.

TABLE 1

| RUN # | Number of Saline Washes | Days in Culture | Total Cell # | Intracapsular Ab Conc. µg/ml |
|---|---|---|---|---|
| 441A | None | 20 | $4.3 \times 10^7$ | 360 |
| 441B | 1 | 20 | $5.0 \times 10^7$ | 560 |
| 441C | 2 | 20 | $7.2 \times 10^7$ | 702 |
| 441C | 3 | 20 | $6.5 \times 10^7$ | 717 |

As may be seen from the data compiled in Table 1, using two or three saline washes produced the highest cell count and the highest intracapsular antibody concentration. More specifically, after three premembrane formation washes with saline, the culture grew about 50% more cells and produced almost double the intracapsular antibody concentration as the culture which was not washed in saline. This experiment illustrates that premembrane formation washing with saline improves the capsules so that the encapsulated hybridomas are healthier and produce more antibody.

From the foregoing it will be apparent that in view of this disclosure those skilled in the art will be able to design specific encapsulation techniques which will consistently produce uniform capsule membranes having permeability properties tailored for specific applications using emperical procedures. Thus, by astute exploitation of the encapsulation parameters disclosed herein, the artisan can produce capsules which will permit free transport through the membrane of molecules up to a selected molecular weight, permit hindered transport of molecules in a range above that weight, and preclude traverse of molecules of a molecular weight and related effective molecular dimensions above the range. Once the procedure has been developed, it can be practiced to manufacture as many capsules as desired for the purpose intended.

In designing a precedure to produce capsules of a specific permeability behavior, the following should be used as general guiding principles. The gel expansion step improves capsule membrane uniformity and increases the effectiveness of the porosity control techniques. Increases in the charge density of the polycationic membrane forming polymers generally produce smaller pores. Increases in the molecular weight of the polycationic polymer generally produce larger pores and thinner membranes. Increases in the duration of the exposure of the polycationic polymer to the gel masses produce a thicker, less permeable membrane. The deposition of a second polycationic polymer over the first reduces the pore size. Expansion of the gel by hydration after membrane formation increases the porosity and contraction decreases porosity. When designing capsules for implantation, a post-coating with a polyanionic polymer is desirable and physiologically incompatible membrane forming materials which cause inflamation or fibroblastic overgrowth should be avoided. When designing capsules for culturing cells, reliquification is desirable and is best conducted using EGTA.

Accordingly, the invention may be embodies in other specific forms without departing from the scope thereof and all of the foregoing embodiments should be considered illustrative. Other embodiments are within the following claims.

What is claimed is:

1. A process for encapsulating a core material within an intracapsular volume defined by a permeable membrane, said process being adapted to improve membrane uniformity and porosity control, said process comprising the steps of:
   A. Gelling a water soluble polyanionic alkali metal alginate polymer containing a core material with an aqueous solution comprising polyvalent cations to form hydrated, dicrete, shape-retaining gelled masses containing said core material;
   B. Expanding said gelled masses by contacting the masses with an aqueous saline solution essentially free of polyvalent cations and having a monovalent cation concentration effective to remove a portion of said polyvalent cations and further hydrate said gelled masses;
   C. Forming a membrane about said expanded gelled masses to form capsules by reaction between anionic groups on said alkali metal alginate and cationic groups on a polycationic polymer having a molecular weight greater than 3,000 daltons.

2. The process of claim 1 comprising the additional step of:
   coating the membrane formed in step C with a water soluble polyanionic polymer by reaction with residual cationic sites on said membrane.

3. The process of claim 1 comprising the additional step of:
   Reliquifying said gelled masses after membrane formation.

4. The process of claim 3 whereby said reliquifying step comprises exposing the capsules to a chelating agent.

5. The process of claim 4 wherein said chelating agent comprises ethylene glycol bis-($\beta$-amino ethyl ether) - N, N-tetra-acetic acid or a salt thereof.

6. The process of claim 1 comprising the additional step of:
   Forming a second membrane layer about the membrane formed in step C by reaction with a second polycationic polymer.

7. The process of claim 6 comprising the additional step of:
   coating said second membrane layer with a water-soluble polyanionic polymer by reaction whith residual cationic sites on at least one of said polycationic polymers.

8. The process of claim 7 comprising the additional step of:
   Reliquifying said gelled masses after membrane formation.

9. The process of claim 8 wherein said reliquifying step comprises exposing said capsules to a chelating agent.

10. The process of claim 9 wherein said chelating agent is ethylene glycol bis-($\beta$-amino ethyl ether) N,N-tetra-acetic acid or a salt thereof.

11. The process of claim 1 wherein said polyanionic polymer is an acidic polysaccharide.

12. The process of claim 11 wherein said acidic polysaccharide is an alginate salt.

13. The process of claim 1 wherein said polycationic polymer is selected from a group consisting of proteins comprising plural reactive nitrogen-containing cationic groups, polypeptides comprising plural reactive nitrogen-containing cationic groups, polyvinyl amines, aminated polysaccharides, salts thereof, and mixtures thereof.

14. The process of claim 13 wherein said polycationic polymer is selected from a group consisting of polylysine, polyglutamine, and polyornithine.

15. The process of claim 6 wherein said second polycationic polymer is selected from a group consisting of proteins comprising plural reactive nitrogen-containing cationic groups, polypeptides comprising plural reactive nitrogen-containing cationic groups, polyvinyl amines, polyethylene amines, aminated polysaccharides, mixtures thereof, and salts thereof.

16. The process of claim 15 wherein said second polycatonic polymer is selected from the group consisting of polylysine, polyglutamine, and polyornithine.

17. The process of claim 1 wherein said core material comprises viable cells.

18. The process of claim 17 wherein said viable cells comprise genetically modified cells.

19. The process of claim 18 wherein said genetically modified cells comprise hybridoma.

20. The process of claim 17 wherein said core material comprises viable eukaryotic cells.

21. A process for encapsulating viable cells within an intracapsular volume defined by a membrane substantially impermeable to molecules having a molecular weight greater than about 150,000 daltons and to cells, said process comprising the steps of:
 a. Gelling an aqueous solution of an alkali metal alginated containing viable cells with a solution comprising physiologically compatible polyvalent cations to form discrete, hydrated, shape-retaining gelled masses containing said viable cells;
 b. Expanding said gelled masses by contacting the masses with an aqueous saline solution essentially free of polyvalent cations and having a monovalent cation concentration effective to remove a portion of said polyvalent cations and further hydrate said gelled masses;
 c. Forming membranes about each of said expanded gelled masses to form capsules by reaction between anionic groups on said alkali metal alginate with a first polycationic polymer having a molecular weight greater than about 3,000 daltons; and
 d. Reducing the pore size of said membranes formed in step c by contacting said membranes with a second polycationic polymer.

22. The process of claim 21 wherein said first polycationic polymer is polylysine.

23. The process of claim 21 wherein said first polycationic polymer has a molecular weight less than about 100,000 daltons.

24. The process of claim 21 wherein said second polycationic polymer has a higher cationic charge density than said first polycationic polymer.

25. The process of claim 22 wherein said second polycationic polymer comprises polyornithine.

26. The process of claim 21 further comprising the step of partially neutralizing the ionic charge of said membranes with a neutralizing agent.

27. The process of claim 26 wherein said neutralizing agent comprises 2-N-cyclohexylamino ethane sulfonic acid.

28. The process of claim 21 further comprising the step of contracting said capsules with a solution which dehydrates said gel masses after step C.

29. The process of claim 28 wherein said dehydrating solution comprises a calcium ion solution.

30. The process of claim 21 comprising the step of reliquifying said gel masses by contacting said gel masses with a chelating agent.

31. The process of claim 30 wherein said chelating agent is ethylene glycol bis-($\beta$-amino ethyl ether)-N,N-tetra-acetic acid or a salt thereof.

32. The process of claim 21 comprising the additional step of coating said membranes with a water-soluble polyanionic polymer by reaction with residual cationic sites on said membranes.

33. The process of claim 32 wherein the polyanionic polymer for coating comprises alginate.

34. A process for encapsulating a viable cell within an intracapsular volume defined by membrane, said membrane being substantially impermeable to molecules having a molecular weight greater than about 500,000 daltons and to cells, and being permeable to molecules having a molecular weight up to at least 160,000 daltons, said process comprising the steps of:
 1. Gelling an aqueous solution of an alkali metal alginate containing viable cells with a solution comprising physiologically compatible polyvalent cations to form discrete, hydrated, shape-retaining gelled masses containing said viable cell;
 2. Expanding said gelled masses by contacting the masses with an aqueous saline solution essentially free if polyvalent cations and having a monovalent cation concentration effective to remove a portion of said polyvalent cations and further hydrate said gelled masses; and
 3. Forming membranes about said expanded gelled masses to form capsules by contacting the gelled masses with a solution comprising a polycationic polymer having a molecular weight greater than about 3,000 daltons and less than about 100,000 daltons.

35. The process of claim 34 wherein said polycationic polymer is selected from a group consisting of polylysine, polyornithinine, and polyglutamine.

36. The process of claim 35 further comprising the step of partially neutralizing an ionic charge of said membranes formed in step 3 with a neutralizing agent.

37. The process of claim 36 wherein said neutralizing agent comprises 2-N-cyclohexylamino ethane sulfonic acid.

38. The process of claim 34 further comprising the step of contracting said capsules with a solution which dehydrates said gelled masses after step 3.

39. The process of claim 38 wherein said dehydrating solution comprises calcium ions.

40. The process of claim 34 comprising the additional step of coating said membranes with a water-soluble polyanionic polymer by reaction with residual cationic sites on said membranes.

41. The process of claim 40 wherein the polyanionic polymer used for post-coating comprises alginate.

42. The process of claim 34 comprises the additional step of:

Reliquifying the gelled masses by exposing said capsules to ethylene glycol bis-($\beta$-amino ethyl ether)-N, N-tetra-acetic acid or salts thereof.

43. A process for encapsulating viable cells within an intracapsular volume defined by a membrane, said membrane being permeable to molecules having a molecular weight greater than 500,000 daltons and being impermeable to cells, said process comprising the steps of:

i. Gelling an aqueous solution of an alkali metal alginate containing viable cells with a solution comprising physiologically compatible cations to form discrete, hydrated, shape-retaining gelled masses containing said viable cells;

ii. Expanding said gelled masses by contacting the masses with an aqueous saline solution essentially free of polyvalent cations having a monovalent cation concentration effective to remove a portion of said polyvalent cations and further hydrate said gelled masses; and iii. Forming a membrane about said expanded gelled masses to form capsules by contacting the gelled masses with a polycationic polymer having a molecular weight greater than about 200,000 daltons.

44. The process of claim 43 comprising the additional step of coating said membranes with a water-soluble polyanionic polymer by reaction with residual cationic sites on said membranes.

45. The process of claim 44 wherein said polyanionic polymer comprises alginate.

46. The process of claim 43 comprising the additional step of:

Reliquifying the gelled masses by exposing said capsules to a chelating agent.

47. The process of claim 46 wherein said chelating agent is ethylene glycol bis-($\beta$-amino ethyl ether)-N, N-tetra-acetic acid or a salt thereof.

48. The process of claim 43 wherein said viable cells comprise IgM excreting cells and said membranes are permeable to IgM.

49. In a cell culturing technique comprising the steps of enveloping at least one cell to be cultured in a polyanionic, polyvalent cation cross-linked, shape-retaining alginate gel mass, forming a semipermeable membrane about said gel mass to form a capsule by contact with a polycationic polymer having a molecular weight greater than about 3,000 daltons, reliquifying the gel mass, and culturing the cell within the capsule, the improvement wherein:

said alginate gel mass, before contacting with the polycationic polymer to form a semipermeable membrane, is expanded by contact with an aqueous saline solution essentially free of polyvalent cations and having a monovalent cation concentration effective to remove a portion of the polyvalent cation crosslinking said alginate gel and further hydrate said alginate gel mass; and said reliquifying step is conducted by exposing the capsule to an aqueous solution of ethylene glycol bis-tetra-acetic acid.

50. The technique of claim 49 wherein said polycatronic polymer is polylysine.

51. The technique of claim 49 wherein said polycatronic polymer is polyornithine.

* * * * *